United States Patent
Park

(10) Patent No.: US 8,256,040 B2
(45) Date of Patent: Sep. 4, 2012

(54) METHOD AND COMPOSITIONS FOR BATH

(76) Inventor: Soo Kyoung Park, East Rutherford, NJ (US)

(*) Notice: Subject to any disclaimer, the term of this patent is extended or adjusted under 35 U.S.C. 154(b) by 0 days.

(21) Appl. No.: 13/159,342

(22) Filed: Jun. 13, 2011

(65) Prior Publication Data
US 2011/0271974 A1 Nov. 10, 2011

Related U.S. Application Data

(62) Division of application No. 11/503,199, filed on Aug. 11, 2006, now abandoned.

(51) Int. Cl.
*A47K 3/00* (2006.01)

(52) U.S. Cl. .......................... 4/541.1; 510/130

(58) Field of Classification Search .................. 4/541.4; 510/130
See application file for complete search history.

(56) References Cited

U.S. PATENT DOCUMENTS

| | | | |
|---|---|---|---|
| 5,289,599 A * | 3/1994 | Hintz et al. | 4/613 |
| 6,080,708 A * | 6/2000 | Glenn et al. | 510/130 |
| 6,281,177 B1 * | 8/2001 | Moriyama | 510/130 |

* cited by examiner

*Primary Examiner* — Tuan N Nguyen
(74) *Attorney, Agent, or Firm* — Park & Associates IP Law, P.C.

(57) ABSTRACT

A method of foot care for a bather comprises: providing a water container partially filled water therein; adding a first material to the water, the first material including a super absorbent polymer capable of absorbing a substantial amount of water; forming a gelatinous mixture with the first material absorbing the water; placing the feet of the bather in the gelatinous mixture for bathing; adding a second material and water to the gelatinous mixture, the second material including a dissolving agent for transforming the gelatinous mixture to a liquid having a low viscosity and a sanitizing or disinfectant agent for sanitizing without causing toxic effects to the bather; placing for bathing the feet of the bather in the dissolved liquid; and, removing the dissolved liquid from the water container.

9 Claims, 5 Drawing Sheets

METHOD AND COMPOSITIONS FOR BATH

REFERENCE TO RELATED APPLICATIONS

This is a divisional application of U.S. patent application Ser. No. 11/503,199 filed on Aug. 11, 2006, now abandoned.

FIELD OF THE INVENTION

The present invention relates to bathing, and more particularly to methods for bathing and compositions thereof for applying to a bath, particularly for applying to a foot bath, in which the compositions are added in the water of a bath tub for producing gel or jelly-like substance for foot cleansing or treatment purposes and/or to provide a relaxing experience to the bather.

BACKGROUND OF THE INVENTION

It has been well recognized that bathing provides a refreshing and relaxing experience, as well as cleansing of a human body and treatment thereof. Various types of bathing products, devices and methods of utilizing tools and therapeutic substances for bathing are known, such as those using a bathtub, a whirlpool bath or Jacuzzi, and other bathing devices. Many bath products are currently available to enhance the bathing experience. For example, bathing salts may be added to the bath water to add a pleasant aroma or to soften the bath water. There are also numerous scented oils and soaps available for use while bathing. Taking a steaming bath is also known for physiological and psychological benefits such as lowering blood pressure, relaxing muscles, relieving aches and pains and calming the mind. Bathing also cleans the outer layer of the skin by removing surface dirt, oils, and the like.

Foot therapy and foot bathing methods are also known in connection with personal therapeutic use, for foot care, and commercial pedicure procedures, for example. Some of such known devices are capable of producing heat to the water for enhancing blood circulation, and also water jet stream, air bubbles, and vibration in the water for facilitating massage and sensations to the body and/or feet of the bather.

Bathtubs and foot bath devices capable of producing water jet (and optionally air bubbles or stream in addition to the water jet) or whirlpool functions typically have a series of, or one or multiple circulation pipe circuits connected to the bathtub for providing water turbulence to the bathing water. After using the bathtubs, used or treated water needs to be drained as completely as possible and the tubs and bath system are to be cleaned and sanitized before next using. However, the used water as well as other impurity substances stored in the water system and pipes, for example, such as particles, dirt, loosed or removed skin, scum, nail particles and debris, oily substances such as body grease, and other materials, are very hard to be completely removed from the water system and circulation pipes. Such impure substances in the water deposit and continue to build up in the pipes of the whirlpool system and passage sections of the water pump, etc. The used water and impure substances remaining in the bath system and pipes decay as time passes and cause serious harmful, unsanitary and toxicity concerns, typically producing unpleasant odor, germs, bacteria, or other harmful substances to the human. Accordingly, cleaning, sanitization, and deodorizing of the water and bathing system, including the water circulation system, becomes a very important concern, which is particularly more important in commercial operations such as spas and pedicure operations because the bathing devices in the commercial operations are used repeatedly to multiple people with different body and skin conditions.

Among various bathing methods known, bathing in the water containing substances such as a fluffy gel or jelly-like material has been suggested recently. For example, U.S. Pat. No. 6,281,177 to Moriyama discloses a bath jelly product for creating a gelatinous mixture in a bathtub for bathing a human body in the gelatinous mixture. A component containing sodium polyacrylate and other substances are added to hot water to produce a gelatinous mixture for promoting a luxurious and relaxing bathing experience to a bather as well as allowing deep cleansing of skin pores with the component. According to this reference, a second component comprising pure sodium chloride or other salts is suggested to be added to the gelatinous mixture in order to dissolve the mixture and thus for allowing the contents of the tub to be easily drained from the tub typically through a vertical drain pipe disposed at the bottom of the bathtub (as shown in FIG. 6 of the disclosure of U.S. Pat. No. 6,281,177).

The methods suggested in U.S. Pat. No. 6,281,177 relate to bathing of an entire human body in a fluffy jelly-like mixture. This disclosure, however, does not provide any suitable bathing methods and bathing compositions especially useful for foot bathing, more in particular, that are to be used in a whirlpool tub environment having water circulation pipes connected to the bathtub. To the contrary, U.S. Pat. No. 6,281,177 in fact teaches away from utilizing a bath apparatus having such a whirlpool function (see column 4, lines 43-46).

As discussed above, sanitization and cleaning of the used water and impure substances in the bath system and circulation pipes, including water-jet tubes and various valves thereof, is a very important concern to be carefully considered and handled, particularly, in such bathtubs with whirlpool functions.

In addition, it is known in the art that chemical cleaning or detergent agents are typically used for cleaning and sanitization of the bathtubs and bathing systems after the bath is used and before a next use of the bath system. One generally accepted procedure for cleaning the bath system, particularly for those having a whirlpool bathing function, comprises: (i) used water is drained from the bath system after the bath, (ii) the bathtub is filled with clean water, (iii) suitable chemical detergent is added in the water, (iv) the whirlpool system is operated for a substantially long period of time for cleaning the system, and (v) the cleaned water with detergent is drained off. This cleaning procedure is repeated frequently, preferably after each bathing operation. Accordingly, this procedure requires the use of excessive water for the cleaning along with a substantial time and electrical energy consumption for the cleaning operations, in addition to the normal bathing operations.

SUMMARY OF THE INVENTION

Accordingly, in consideration to handle or overcome aforementioned and other shortcomings of the prior art, the present invention is directed to novel methods for bathing, in particular for foot bathing, and compositions to be used for the foot bathing.

More specifically, the present invention is directed to novel methods for bathing, particularly for foot bathing, in a jelly-like substance as well as for subsequent cleaning and sanitizing (including deodorizing) of the bathing system including used water in the system, and the bathtub and circulation pipes, etc. The present invention is also directed to methods for foot bath and its compositions for producing a jell-like substance and also for subsequently dissolving the jelly-like substance while effectively sanitizing and deodorizing the used water and impure substances contained in the water and the bath system, in which the sanitization is to be performed during the normal bathing operations without using harsh chemical cleaning substances. As the primary sanitization of the bath system according to the present invention is performed during the normal bathing operations, it can eliminate or at least substantially reduce the time-consuming, subsequent cleaning operations known in the conventional cleaning procedures. The methods and compositions of the invention may further enhance advantageous foot cares and treatments thereof, and cleansing of the feet for the users with the bathing compositions and also providing relaxing and refreshing bathing experiences to the users.

According to one aspect of the invention, a bathing product for use with a bath apparatus for bathing, comprises: a first material including a super absorbent polymer, the first material being usable for absorbing a substantial amount of water and forming a gelatinous mixture suitable for bathing when the first material is added to a sufficient amount of water; and a second material including sodium chloride and sodium hydrogen carbonate, the second material being usable for transforming the gelatinous mixture to a liquid having a low viscosity when the second material is added to the gelatinous mixture while also facilitating sanitization of the liquid and cleaning of the bath apparatus without causing a toxic effect to a bather for bathing in the liquid and also facilitating enhanced body care or treatment. The first material preferably comprises 50-98% by weight sodium polyacrylate formed in powder form, and the second material preferably comprises about 60-95% by weight sodium chloride and about 5-40% by weight sodium hydrogen carbonate.

According to another aspect of the invention, a method of foot care for a bather comprises: providing a water container partially filled water therein; adding a first material to the water, the first material including a super absorbent polymer capable of absorbing a substantial amount of water; forming a gelatinous mixture with the first material absorbing the water; placing the feet of the bather in the gelatinous mixture for bathing; adding a second material and water to the gelatinous mixture, the second material including a dissolving agent for transforming the gelatinous mixture to a liquid having a low viscosity and a sanitizing agent for sanitizing without causing toxic effects to the bather; placing for bathing the feet of the bather in the dissolved liquid; and, removing the dissolved liquid from the water container. According to one preferred embodiment, the first material comprises 50-98% by weight sodium polyacrylate and the second material comprises 60-95% by weight sodium chloride and 5-40% by weight sodium hydrogen carbonate and wherein 20-70 grams of the first material is added to 1-2 gallons of water to form the gelatinous mixture, and wherein 40-100 grams of the second material and 3-7 gallons of water are added to the gelatinous mixture to form the dissolved liquid.

DETAILED DESCRIPTION OF THE INVENTION

With reference to the drawings, a bath apparatus, in particular a foot bath apparatus or pedicure system, methods of foot bathing and pedicure treatments, and compositions for that are described and illustrated herein according to the principles of the invention. Even though the present invention is particularly described in connection with pedicure or foot bathing systems and related methods thereof, it is not limited thereto and may be applied to beauty care applications and bathing for the entire body of a user.

Figure 1:
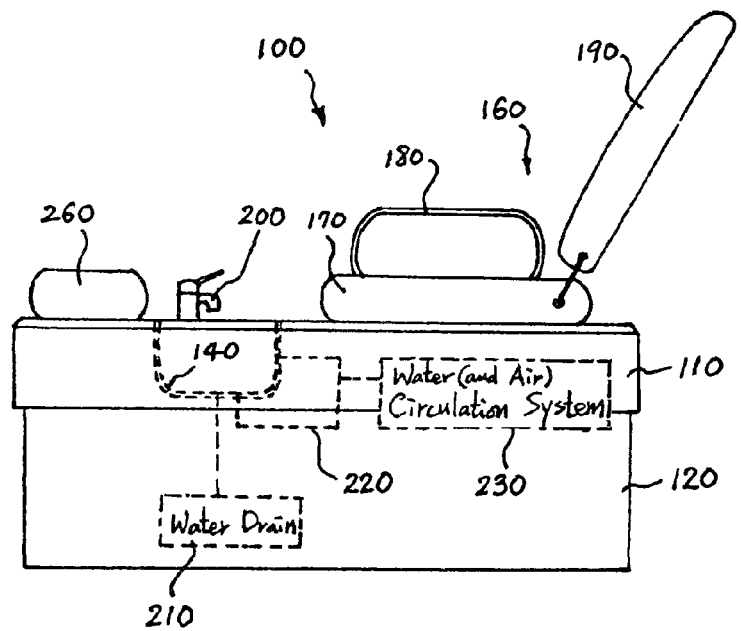
FIG. 1 is a side schematic representation of a foot bath apparatus or so-called pedicure treatment system, constructed according to the principles of the present invention.
Figure 2:
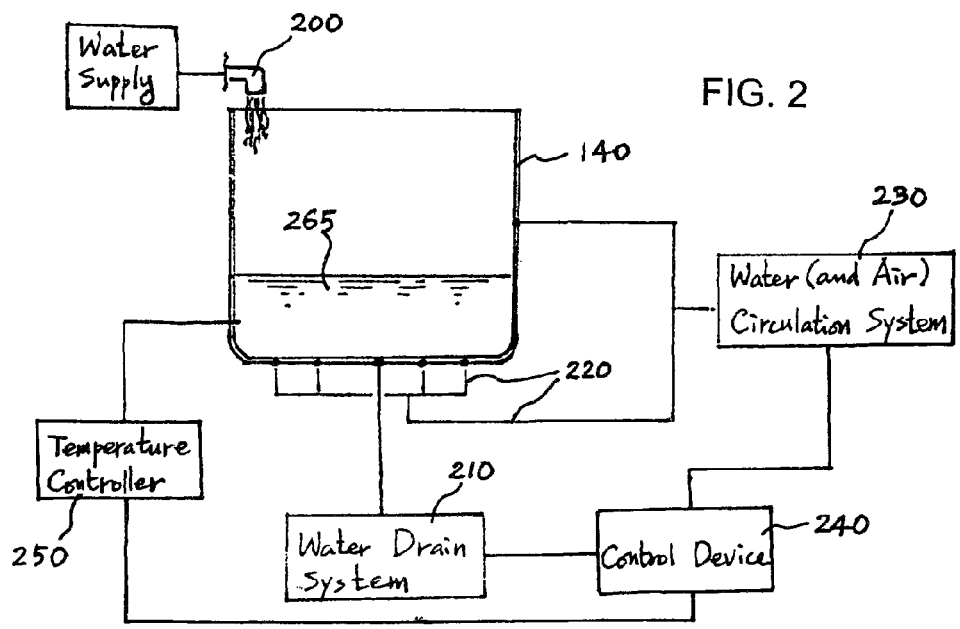
FIG. 2 is a schematic diagram of a portion of the foot bath apparatus of FIG. 1, illustrating the bathtub is being filled with hot water before performing the foot bath.

Referring to FIGS. 1 and 2, the foot bath apparatus or so-called pedicure treatment system 100 of the present invention is depicted herein as one way of example for illustrating the principles of the invention, in which the apparatus can be suitably used for commercial pedicure operations and as well as personal foot care uses at home. However, the foot care and pedicure methods and compositions described in this invention disclosure can also be used with other conventional bathing devices of known type, or with other pedicure and foot care devices.

The foot bath apparatus or pedicure system 100 typically includes, a housing 110 having an upper housing portion 110 and a lower housing portion 120. A bathtub or water receptacle 140 is disposed at a suitable exposed location on the upper housing portion 110. A user occupying seat 160 (preferably having a bottom cushion 170, a pair of arm rests 180, and back support 190) is conveniently disposed at the upper housing portion 110 for facilitating immersion of their feet in bathtub 140 while the bather is seated on the seat 160. One or plural water supply devices with water faucets 200 are provided for supplying water to the bathtub 140. Although system 100 could be operated in a quiescent or non-jetted mode, it is generally preferred that a recirculation system be provided to move fluids within the bathtub 140 with a jet action of water and/or air stream when it is desired to use, as will be further described later in detail. Mechanical and plumbing systems for re-circulation and other operations are located within lower housing 110. A water drain or receptacle outlet 210, a re-circulating circuit 220, and a water (and optionally air as well) circulation system 230 operating under control of a control device 240 (such as micro-computer or other programmable control device) are also provided for appropriate operation of the bath apparatus and the whirlpool system thereof. The apparatus 100 may also includes a temperature controller 250 for heating and maintaining the water in the bathtub to a suitable temperature for bathing. The apparatus 100 further preferably includes one or a pair of foot rests 260 at suitable location for placing the feet of the bather thereon whenever desired during the bathing operation.

Referring to FIGS. 2-9, the bathing operation using the apparatus 100 and composition of the bathing product of the invention are described herein. The apparatus 100 is to be used with the bathing product of the invention, which includes two bathing packages provided preferably in the form of a cardboard box or other suitable container, namely a first package for retaining a first material and a second package for a second material. The first material contained in the first package is preferably in the form of powder or particles, and usable for application to a bathtub of hot water to form a gelatinous mixture. Likewise, the second material contained in the second package is preferably in the form of powder or particles, which is usable for application to the tub of gelatinous mixture to dissolve the mixture into a relatively non-viscous liquid. The second material further includes other utility and functions to be described later in detail. Operating instructions are typically printed on the side of the packaging and as well as on a separate instruction sheet packaged within the product package. The actual amount in the packages can be varied in a manner suitable either for a single use or for multiple uses for using with exact measuring in each use.

The chemical compositions of the product will now be described. The first material of the present invention is preferably formed in the form of powder or small particles, and comprises as a principal ingredient a super absorbent material which is known to be a water-absorbing, water-swellable, water-insoluble material including an organic or inorganic absorbent polymer capable of absorbing many times, preferably more than about five to ten times its weight of water. Candidates for the super absorbent materials of the invention include, but without limitation thereto, sodium polyacrylate, polyacrylic acid, polyvinyle amine salt, polyvinyle amine, and combinations thereof, and other nontoxic polymeric materials capable of absorbing many times of water and swelling without dissolving into the water.

According to one preferred embodiment, the first material of the present invention comprises about 50-98% by weight a super absorbent material such as sodium polyacrylate that is suitable for forming a smooth and fluffy gel-like mixture when applied in the water and also known to be non-toxic and harmful to the human body. The first material may further comprise about 5-50% by weight of organic or inorganic materials for facilitating beauty care, treatments for the human body and feet, cleansing of the skin, or adding refreshing and relaxing experience. According to another preferred embodiment, the first material is selected to include about 60-95% by weight sodium polyacrylate, about 1-40% by weight herbal or plant extracts or derivatives thereof known to be useful for enhancing skin care, and other additives such as small amount of fragrance and coloring agent, etc. Candidates for the plant extracts or derivatives thereof include, without limitation thereto, aloe vera, cucumber, olive, rosemary, lavender, thyme, green tea, black tea, and mint.

In one example, the first material is selected to include about 60-95% by weight sodium polyacrylate, about 1-20% by weight aloe vera extract, about 1-20% by weight cucumber extract, about 0.1-3% by weight of fragrance, and about 0.1-3% by weight of coloring agent. In another example, the first material is selected to include about 60-95% by weight sodium polyacrylate, about 1-30% by weight of aloe vera or cucumber extract, about 1-15% by weight urea, about 0.1-3% by weight of fragrance, and about 0.1-3% by weight of coloring agent. Among the plant extracts, aloe vera extract typically obtained from its leaves and cucumber extract are useful for advantageous skin care, for example, promoting healing of damaged or heat-burned skin, and urea (also known as carbamide) is useful for softening and cleansing the skin. The amount of the herbal or plant extracts may be varied in a great degree, and that of the fragrance and coloring agent may be eliminate completely. Moreover, other additional ingredients of suitable amounts about such as L-mentol, vitamin A, vitamin C, and vitamin E, may be added in the first material for enhancing advantageous skin care and/or refreshing experience. Each additional ingredient is preferably 0.1-5% by weight, but can be varied.

The second material of the invention is preferably formed in the form of powder or small particles, and comprises suitable amounts of sodium chloride and sodium hydrogen carbonate as major ingredients thereof. According to one preferred embodiment, the second material of the present invention comprises about 60-95% by weight pure sodium chloride (but other salts may also be used instead thereof or in addition thereto), and about 5-40% by weight sodium hydrogen carbonate (which is also known as sodium bicarbonate or baking soda). The second material may also comprise about sixty to ninety-five percent by weight sodium chloride with small amounts of other salts added thereto. Among the ingredients, sodium chloride (and/or other salts) functions for dissolving the gel-like mixture of the first material with water and transforming it to a liquid having a low viscosity in order to allow the contents of the tub to be easily drained from the bath apparatus having drain pipes. Sodium hydrogen carbonate functions for facilitating sanitization of the liquid and also for cleaning of the bath apparatus including the bathtub and drain pipes without causing any toxic or harmful effect to a bather for bathing in the liquid. Moreover, sodium hydrogen carbonate added in the bathtub water may also be beneficial to the bather. For example, it also functions for deeply cleansing the skin by removing scum, body oil, and grease from the skin and sweat capillaries, absorbing calcium, magnesium and metallic material from the water and transforming the acidified water to the neutral bathing water having enhanced pH value beneficial to the skin, removing bad smells and deodorizing the skin and bathing water, relieving the irritated skin, relieving sufferings from irritating atopic skin and sunburned skins, and prickly heat in the skin, and enhancing blood circulation in the skin. Accordingly, the sodium hydrogen carbonate components in the bathing water may provide various skin care and therapeutic benefits while without irritating or giving harmful effects to the bather.

In addition to sodium chloride and sodium hydrogen carbonate discussed above, the second material of the present invention may further comprise chloramines (preferably monochloramine such as Chloramine-T) or chlorine of suitable amounts for facilitating further sanitization of the dissolved liquid without adding toxicity to the bather. According to one preferred embodiment, the second material of the bathing product of the invention includes about 60-95% by weight sodium chloride, about 5-40% by weight sodium hydrogen carbonate, and about 0.1-15% by weight monochloramine. Germs, bacteria, and other infective substances in the dissolved liquid can effectively be killed or disinfected by such addition of chloramines or chlorine products known to be used as disinfectants. Thus, by application of the second material containing sodium hydrogen carbonate (i.e., baking soda) and chloramine or chlorine, the dissolved liquid can become safer disinfected bathing water, that is more beneficial especially for commercial pedicure operations in which the bath apparatus is frequently used to multiple clients.

Moreover, the above-mentioned other ingredients of the first material, such as fragrance, coloring agent, urea, L-mentol, vitamin A, vitamin C, and vitamin E, may also be added in the second material for enhancing advantageous skin care or refreshing experience.

FIG. 2 illustrates the process of filling bathtub 140 with hot water 265 by a faucet 200, before bathing of the feet therein. The hot water produces stream and preferably has a temperature of approximately 40 degrees Celsius (104 degrees Fahrenheit). For purposes of the present invention, temperatures in a range of 30 to 50 degrees Celsius will allow the gelatinous mixture to form correctly. If the water is not hot enough, the gelatinous mixture will not form. If the water is too hot, a bather may be scalded. Temperatures of over about 50 degrees Celsius typically will scald a bather, that may however be varied depending on the person.

Bathtub 140 typically is filled with hot water 265 to about one third or one fourth the capacity of the bathtub for foot bathing, namely approximately one to two gallons of hot water, before the addition of the first material as described above. A ratio of one to two gallons of hot water is used for approximately 20-70 grams of the first material. This ratio may also be described as within a range of about 0.01 to 0.1 gallons of water per gram of the first material. Other amounts of water may be used depending on the size of the bathtub and so long as this water to first material ratio range is maintained to produce a generally gel-like mixture.

Figure 3:
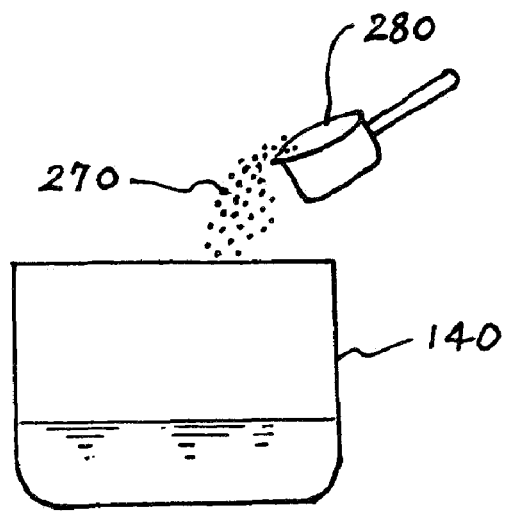
FIG. 3 is a schematic diagram of a portion of the foot bath apparatus of FIG. 1, illustrating the process of adding a first material to the bathtub filled with hot water for producing a gelatinous mixture for foot bathing therein.
Figure 4:
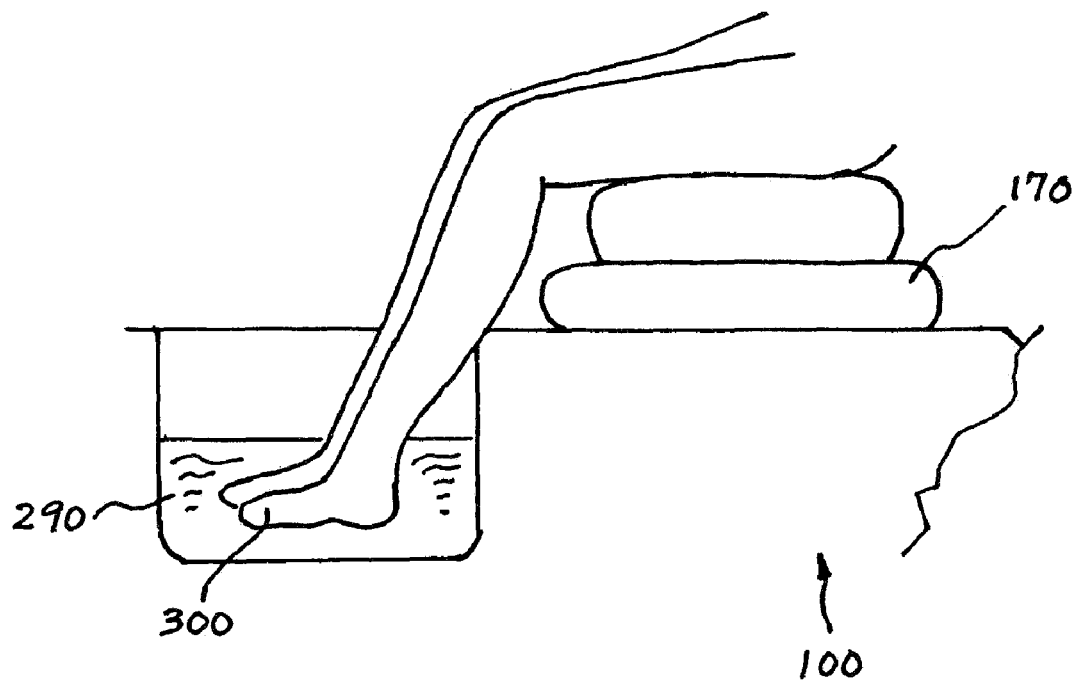
FIG. 4 is a schematic diagram of a portion of the foot bath apparatus of FIG. 1, illustrating the process that the feet of a user is seated in the bathtub containing the gelatinous mixture.

FIG. 3 is a schematic view illustrating a portion of the foot bath apparatus and the process of applying a first material 270 to the bathtub filled with hot water 265. The first material 270 of between about 20 and 70 grams, which may be varied depending on preference of the bather, is filled in a suitable measuring cup 280 and added to tub 140 filled with hot water 265 after the tub reaches one to two gallons of hot water. The material/water mixture is then gently stirred to facilitate even mixing of the material throughout the hot water. After several minutes the hot water/material mixture will have become a gelatinous mixture 290 (FIG. 4). The actual time periods may be varied depending on the amount of the first material to be added and also that of the water contained in the tub. At this point the gelatinous mixture 290 is ready for bathing.

Referring now to FIG. 4, a foot bathing process is illustrated herein. When the gelatinous mixture is ready for bathing, a bather is seated in the seat 160 and the feet 300 of the bather are placed in the gelatinous mixture 290 of the tub. The feet 300 of the bather are substantially or at least partially submerged in gelatinous mixture 290. Once the feet of the bather is seated in the bathtub the level of the gelatinous mixtures rises due to the volume of the feet within the tub, and the gelatinous mixture substantially covers the feet of the bather. The feet typically will remain substantially or partially submerged in gelatinous mixture 290 for approximately five to ten minutes or longer depending on the preference and desire. During the time the feet are soaking in tub 110, the gelatinous mixture removes water, sweat and toxins from below the uppermost surface layers of the bather's skin, as is described more fully by U.S. Pat. No. 6,281,177, the contents of which are incorporated herein by reference. The temperature of the mixture 290 may be maintained by the temperature controller 250 to a suitable bathing temperature. With the feet submerged in the warm and soft gelatinous mixture, the bather may experience entirely refreshing and relaxing feelings while the feet are cleansed deeply. Moreover, when the first material 270 includes materials derived from various useful plant extracts described above (e.g., aloe vera and cucumber), the skin of the bather can be further treated by the beneficial ingredients of the plants.

Figure 5:
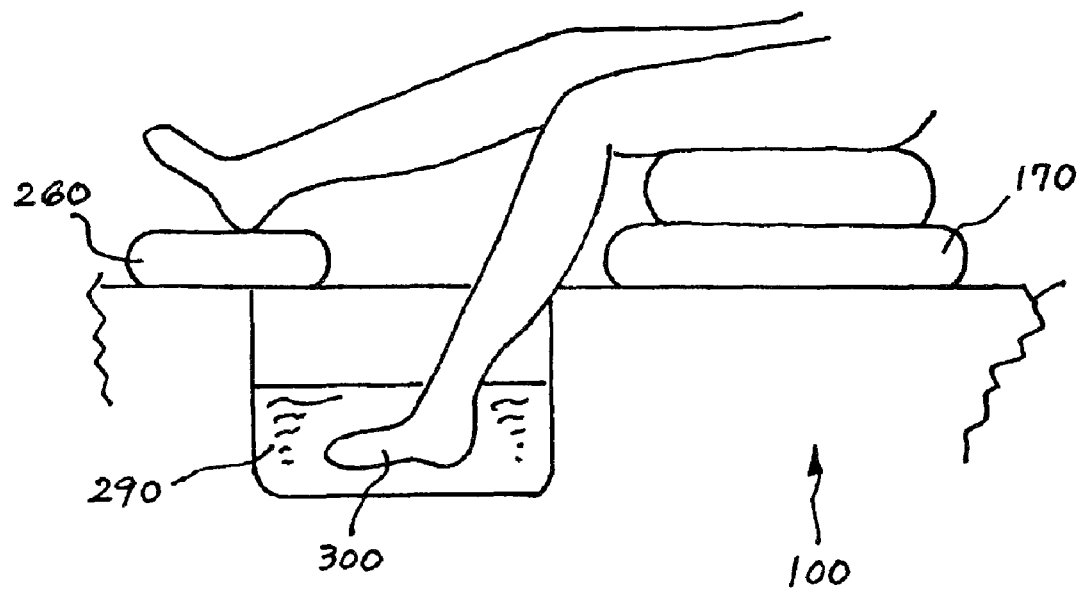
FIG. 5 is a schematic diagram of a portion of the foot bath apparatus as shown in FIG. 4, illustrating the process that one foot of the user is seated in the bathtub of the gelatinous mixture and the other one is placed on a side foot support of the foot bath apparatus for pedicure or foot care services.

Referring to FIG. 5, an optional foot care process in addition to the foot bathing process described above with FIG. 4 is described herein. This optional process is particularly suitable for commercial pedicure operations and personal foot care operations as well. After the feet of the bather have been soaked for the desired amount of time, one foot 300 of the bather is exited from the mixture 290 and placed on the foot rest 260. Then, the foot on the foot rest 260 is massaged and treated by known methods. For example, the foot is squeezed with hands, spots of the foot are pressed with fingers or other pressing devices, or placed on a foot vibrator for heath treatments. In addition, conventional commercial pedicure treatment procedures may optionally further be performed onto the foot, such as filing toenails, removing old polish on toenails and applying new polish, removing cuticles and callous in the toes, applying steam to the foot, and massaging with oil, etc. However, such optional pedicure treatments are typically to be performed in a later process to be described in connection with FIG. 8. Then, the treated foot 300 is returned to the mixture 290, and the other foot is exited from the mixture 290 and placed on the foot rest 260. Similar operations and treatments described above are applied onto the switched foot. This foot care process can last approximately about five to ten minutes or longer depending on the preference and desire of the bather. Moreover, after this process the two feet of the bather can be seated again in the warm mixture 290 for a suitable period of time, as shown in FIG. 4, if desired.

Figure 6:
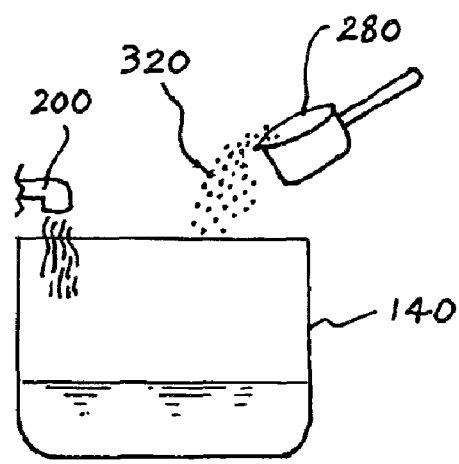
FIG. 6 is a schematic diagram of a portion of the foot bath apparatus as shown in FIG. 4, illustrating the process of adding a second material to the bathtub of the gelatinous mixture for dissolving and further treating the gelatinous mixture, while also adding hot water in the tub.

Referring to FIG. 6, after the feet 300 of the bather have exited tub 140, the second material 320 described above is added to the gelatinous mixture 290 along with fresh hot warm water for dissolving the mixture and further treating the dissolved liquid. More specifically, approximately 40-100 grams of the second material 320 are added to approximately one to two gallons of gelatinous mixture 290, and three to seven gallons of hot water (preferably of about 40 degrees Celsius) are added thereto through the faucet 200. The mixture is then gently stirred to facilitate even mixing of the second material and water throughout the gel-like material. After approximately five to ten minutes the gelatinous mixture will have become a relatively non-viscous liquid 330 (FIG. 7) in a state that can be easily drained from tub 140 through the drain 210 of the apparatus. As described above, sodium chloride or other salts in the second material functions as a dissolving or dissolution agent, while sodium hydrogen carbonate in the second material facilitates sanitization of the dissolved liquid and cleaning of the bath apparatus 100 without causing a toxic effect to a bather for bathing in the liquid. To the contrary, sodium hydrogen carbonate in the second material enhances therapeutic or body care benefits for the bather, as described before. Moreover, the second material 320 may include disinfectant agents such as chloramine for further sanitizing the liquid while without irritating the feet for bathing therein.

Figure 7:
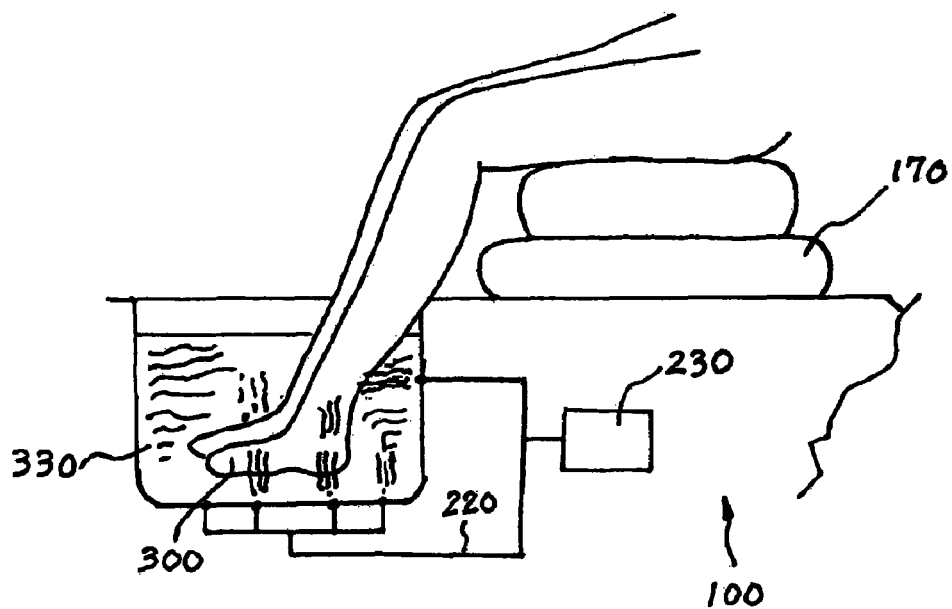
FIG. 7 is a schematic diagram of the foot bath apparatus as shown in FIG. 4, illustrating the process that the feet of the user is seated for further bathing treatments in the bathtub filled with the hot water added, dissolved mixture while operating the whirlpool function of the apparatus.

Referring to FIG. 7, the feet 300 of the bather is now seated for further bathing treatments in the bathtub 140 filled with the dissolved liquid which is thoroughly mixed with hot water. Bathing in this non-viscous liquid 330 enhances further cleansing and therapeutic effects to the body as discussed above. The whirlpool function of the apparatus 100 is preferably turned on during the bathing, and the liquid is recirculated through the circulation circuits 220 and water stream (optionally with air bubbles or stream) is repeatedly injected onto the feet. This further enhances the bathing operation to the bather, while also sanitizing the bathing liquid 330 in the system and the bath apparatus 100 including the bathtub 140, circulation circuits 220, and circulation system 230, with the aid of sodium hydrogen carbonate in the second material and optionally also of chloramine as discussed above. The feet and lower legs are seated and submerged in whirlpool bath for approximately five to twenty minutes or longer depending on the preference and desire.

Figure 8:
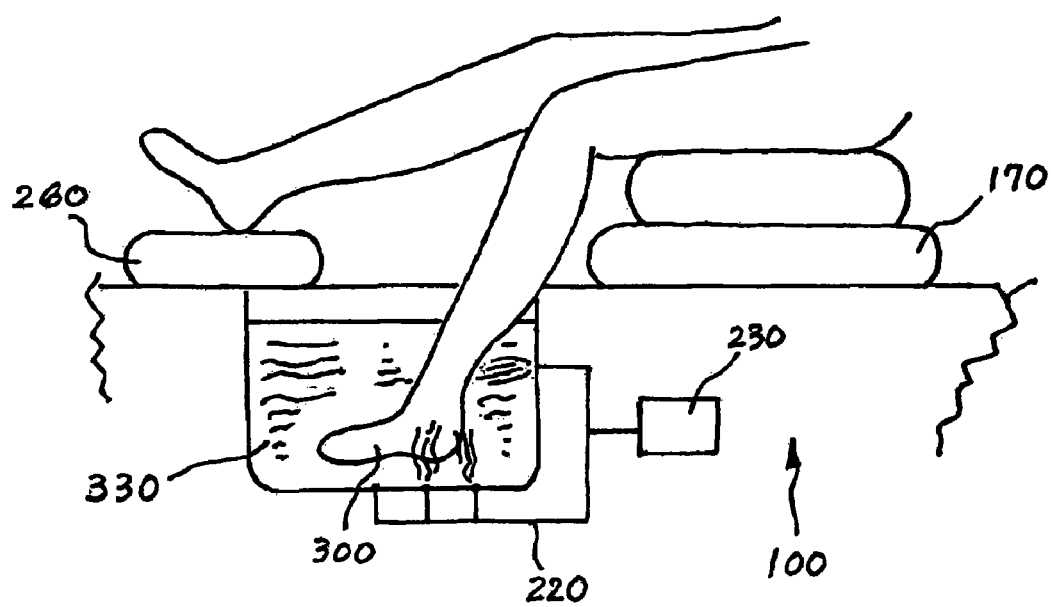
FIG. 8 is a schematic diagram of the foot bath apparatus as shown in FIG. 7, illustrating the process that one foot of the user is seated in the bathtub of the tub and the other one is placed on a side foot support of the foot bath apparatus for pedicure or foot care services.

During this bathing operation, each foot may be exited in turn and placed on the foot rest 260 as illustrated in FIG. 8. Further pedicure or foot care operations such as massaging and pressing the feet, vibrating with a vibrator, and conventional commercial pedicure treatments such as filing toenails, removing old polish on toenails and applying new polish, removing cuticles and callous in the toes, applying steam to the foot, and massaging with oil or lotion, etc. These optional pedicure treatments can be performed before as described in connection with FIG. 5. However, it is more preferable that these treatments are to be performed at the present process.

Figure 9:
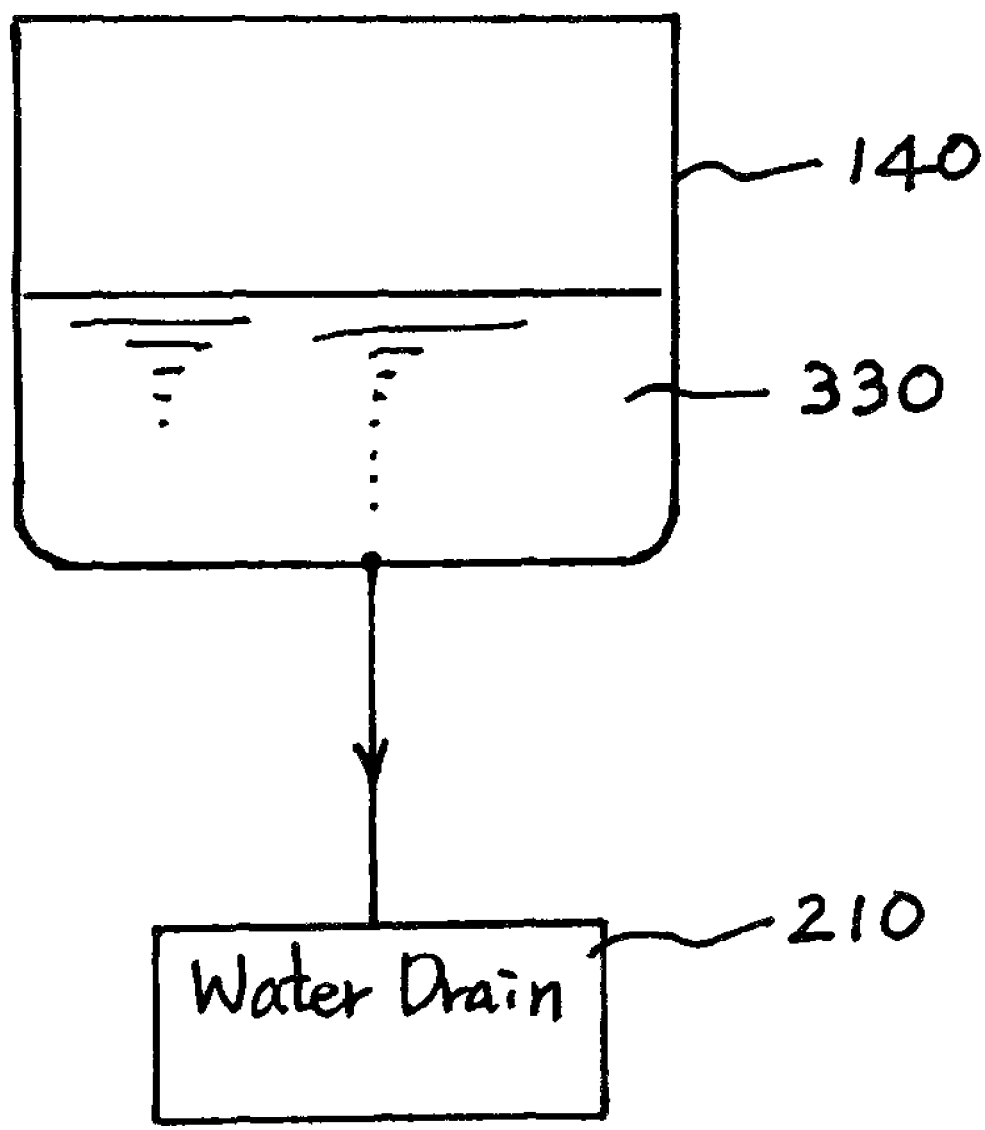
FIG. 9 is a schematic diagram of the foot bath apparatus as shown in FIG. 7, illustrating the process that the dissolved mixture is being drained through a water drain system of the apparatus.

The feet of the bather are cleaned with fresh water and soap, and the bathing and pedicure operation ends. Then, as shown in FIG. 9, the low-viscosity liquid in the bathtub is drained from the apparatus 100. Once the gelatinous mixture is mixed with warm water and has transformed to relatively non-viscous liquid 330, having a viscosity very similar to that of water, the liquid may easily be drained from tub 140 through a bath drain 210. After draining of the tub, it may be preferable that the tub 140 is filled with fresh warm water with the faucet 200 (optionally with commercial detergents added to the water depending on the cleaned condition of the apparatus 100), and the whirlpool function of the apparatus 100 is operated for a short period of time (e.g., for a few minutes) and the water circuits 220 and water circulation system 230 is washed off with the warm water to clean the system. However, as described above, because sodium hydrogen carbonate (and optionally with chloramine) in the second material cleans, sanitizes and deodorizes the liquid and the water system of the apparatus 100 during the above-described normal bathing operations, this additional cleaning process may be entirely eliminated or the time period of the cleaning operation may be substantially reduced comparing to the conventional cleaning process which typically requires a substantially long period of time while applying harsh chemical detergent in the water. In addition, according to the invention, such conventional application of harsh chemical detergent my entirely be eliminated or the amounts can be substantially reduced.

While preferred embodiments of the present invention have been shown and described, it will be apparent to those skilled in the art that many changes and modifications may be made without departing from the invention in its broader aspects. The appended claims are intended to cover, therefore, all such changes and modifications as fall within the true spirit and scope of the invention.

What is claimed is:

1. A method of foot care for a bather, comprising:
   providing a bath apparatus with a water container connected to a water circulation system;
   partially filling water in the water container;
   adding a first material to the water, the first material including a super absorbent polymer capable of absorbing a substantial amount of water;
   forming a gelatinous mixture with the first material absorbing the water;
   placing the feet of the bather in the gelatinous mixture of the water container for bathing;
   adding a second material and water to the gelatinous mixture, the second material including a dissolving agent for transforming the gelatinous mixture to a liquid having a low viscosity and a sanitizing agent for sanitizing without causing toxic effects to the bather;
   placing the feet of the bather in the dissolved liquid for further bathing treatment to enhance further cleansing and therapeutic effects;
   circulating the dissolved liquid with the water circulation system while bathing in the dissolved liquid such that a water passage of the bath apparatus can be sanitized by the sanitizing agent of the second material and also providing further bathing treatment; and
   draining the dissolved liquid from the water container through a bath drain of the bath apparatus.

2. The method of claim 1, wherein the super absorbent polymer of the first material comprises sodium polyacrylate.

3. The method of claim 1, wherein the dissolving agent of the second material comprises sodium chloride, and the sanitizing agent comprises sodium hydrogen carbonate or chloramine.

4. The method of claim 1, wherein at least one of the first material and the second material comprises plant extracts or derivatives thereof for facilitating foot care.

5. The method of claim 1, further comprising exiting one foot of the bather from the gelatinous mixture for providing enhanced foot care or pedicure treatments.

6. The method of claim 1, further comprising exiting one foot of the bather from the dissolved liquid for providing enhanced foot care or pedicure treatments.

7. The method of claim 1, wherein the first material comprises 50-98% by weight sodium polyacrylate and the second material comprises 60-95% by weight sodium chloride and 5-40% by weight sodium hydrogen carbonate and wherein 20-70 grams of the first material is added to 1-2 gallons of water to form the gelatinous mixture, and wherein 40-100 grams of the second material and 3-7 gallons of water are added to the gelatinous mixture to form the dissolved liquid.

8. The method of claim 1, wherein the first material comprises 50-98% by weight sodium polyacrylate in powder form.

9. The method of claim 8, wherein the second material comprises 60-95% by weight sodium chloride and 5-40% by weight sodium hydrogen carbonate.

* * * * *